United States Patent [19]

Harding, Jr.

[11] 4,216,669
[45] Aug. 12, 1980

[54] CONTAMINANT ERROR REDUCTION SYSTEM FOR DEW POINT HYGROMETERS

[75] Inventor: John C. Harding, Jr., Watertown, Mass.

[73] Assignee: General Eastern Instruments Corporation, Watertown, Mass.

[21] Appl. No.: 949,017

[22] Filed: Oct. 6, 1978

[51] Int. Cl.[2] .......................................... G01N 25/02
[52] U.S. Cl. ...................................... 73/17 A; 73/29
[58] Field of Search ................. 73/29, 17 A, 335, 336, 73/336.5

[56] References Cited

U.S. PATENT DOCUMENTS

| 2,720,107 | 10/1955 | McBrair | 73/17 A |
| 3,195,344 | 7/1965 | Francisco | 73/17 A |
| 3,623,356 | 11/1971 | Bisberg | 73/17 A |

Primary Examiner—Stephen A. Kreitman
Attorney, Agent, or Firm—Robert F. O'Connell

[57] ABSTRACT

The invention relates to the periodic interruption of normal control at the condensation temperature by cooling the condensing surface to a temperature well below the prevailing dew point for a time sufficient to provide a heavy growth and coalescence of the condensate so as to dissolve all of the soluble material and create a medium by which molecules of solute can migrate. Immediately after cooling, the condensing surface is heated to a temperature well above the prevailing dew point so as to cause total evaporation of the solvent (condensate) and recrystallization or precipitation of the solute into clusters or isolated colonies. The resulting change in mirror reflectance is compensated after total evaporation by automatic adjustment of the light intensity of the source.

15 Claims, 6 Drawing Figures

CONTAMINANT ERROR REDUCTION SYSTEM FOR DEW POINT HYGROMETERS

BACKGROUND OF INVENTION

All optical dew point hygrometers detect the onset of condensation and measure the temperature of the surface where the condensation occurs. All optical dew point hygrometers are susceptible to contaminants collecting on mirror surfaces, which cause a reduction in density of the operating dew layer. This generally reduces the accuracy of the dew point measurement to a degree which depends on the amount of contaminant present and its solubility in water. Both soluble and insoluble materials, if allowed to build up on the condensing surface, will eventually cause the system to go out of control because of reduced mirror reflectance. It has been a common practice as in the Bisberg U.S. Pat. No. 3,623,356 to address the latter (control) problem by either manually or automatically disabling the feedback control system which controls the mirror (condensing surface) temperature and forcing the mirror surface to heat to a dry state, at which time, an additional current is injected into the control loop amplifier at photodetector bridge circuit.

Unfortunately contaminants encountered by optical dew point hygrometers vary widely. One of the most common contaminants are soluble salts in the atmosphere. These salts range from sea salts in coastal areas to limestone in similar geological formations inland. They are always present in the atmosphere and gradually build up on the mirror surface. In addition, these natural contaminants are accompanied and often exceeded by other man-made soluble contaminants, including products of the process under measurement. In the prior art systems, heating of the mirror to the dry state for manual or automatic rebalancing of the optical detection circuit overcomes the loop offset problem associated with reduced reflectance but does not address the problem of measurement error associated with vapor pressure modification as induced by soluble matter. The soluble materials such as salts precipitate out and form a thin layer on the mirror surface. The salts tend to absorb water vapor at temperatures above the dew point and dissolve back into the dew layer when the mirror recools. The temperature of the contaminated mirror therefore does not reach the true dew point even after compensating for the reduced reflectance. The resultant dew layer contains salts which cause the saturation vapor pressure of the dew deposit to decrease, this is in accordance with Raoult's Law. In the absence of soluble contaminants, saturation vapor pressure is a function of temperature only. The dew point is by definition, that temperature where the saturation vapor pressure of the liquid is equal to the partial pressure of the water vapor in the air or carrier gas which is in contact with the liquid. The partial pressure is dependent upon vapor concentration and total pressure only. The equilibrium temperature (dew point) is therefore a true measure of water vapor concentration in the absence of soluble materials, when the total pressure is known. The presence of solute at the site of the condensate causes the instrument to control at a temperature higher than the true dew point. The instrument then displays a higher than actual dew point temperature reading. In a mildly contaminated environment such as might be encountered in an air conditioned area pulling lithium chloride dryers, a typical optical dew point hygrometer will gradually drift upwards, exhibiting an error approaching as much as 3°–4° C. after a few weeks of continuous operation without mirror cleaning. Therefore, the mirror must be periodically cleaned, the interval being selected as a function of the contamination rate and accuracy desired. Usually, cleaning the mirror once a week is adequate to keep the error band of the instrument. In certain instances, where the contamination levels are high, daily cleaning is required. It is therefore a primary object of this invention to provide an instrument where the time required between mirror cleaning for a given rate of contamination and measurement error is extended by orders of magnitude over the required interval for mirror cleaning for prior art instruments.

It is a further object of this invention to provide an instrument where the initial accuracy of the dew-point temperature is maintained despite contamination of the mirror by water soluble materials between cleanings of the mirror.

A further object of this invention is to provide accurate control of the density of the operating dew layer over the specified range of operating conditions.

It is a still further object of the invention to provide automatic compensation of the temperature control loop to eliminate the effects of mirror contamination or variations in the light emitting diodes or photodetectors on the operation of the temperature control loop.

A still further object is to provide totally automatic and unattended operation. All of the operator adjustable parameters; loop gain, dew thickness, loop frequency compensation, and heat pump current limiting which existed in the prior art apparatus are automatically controlled. The manual controls have therefore been eliminated.

It is a feature of this invention that the dew point measurement operation is periodically interrupted by disabling the temperature control servomechanism with the measured dew point being stored in a memory circuit so as not to interrupt the dew point data display.

It is a further feature of this invention that a signal representative of the reduction in mirror reflectance is stored to provide reflectance compensation for said reduction in reflectance during dew point measurement operation. This feature is provided in order that the apparatus be capable of establishing the required operating density of condensate when the instrument is in control at the dew point temperature.

SUMMARY OF THE INVENTION

The dew point temperature measurement servomechanism loop is periodically interrupted by opening the servo loop during which time the measured dew point is stored in a memory circuit to provide a continuous uninterrupted data display. At the time that the temperature control loop is opened, a signal is provided to the temperature control loop to cause the thermoelectric heat pump to provide maximum cooling. After a predetermined length of time, usually a few seconds, a coalescence of the dew on the mirror occurs to form what may be termed a "liquid puddle" on the surface of the mirror. At this time, the temperature control is given a second command to heat the mirror so as to evaporate the heavy layer of condensate which has been formed. As the water evaporates, the liquid puddles break up into smaller puddles which shrink in size, holding higher and higher concentration of soluble contaminant in solution, leaving bare, uncontaminated surface area behind. The individual puddles eventually become saturated and the solute begins to precipitate out, forming polycrystalline clusters or isolated colonies of solute. The net effect is that the soluble material which once formed a continuous sheet across the entire mirror surface is now contained in concentrated colonies which occupy a small fraction of the total surface. After total evaporation of the condensate, the dry but contaminated, mirror reflectance is measured and a compensating signal representative of the amount of reduction in reflection associated with the presence of contamination is stored. This stored quantity is converted to a proportional DC current which is used to adjust the intensity of the light source which illuminates the mirror surface, or to make another equivalent adjustment in the control loop offset. This adjustment compensates for the reduction in mirror reflectance brought about by the presence of contaminants thereby maintaining a preset loop offset. By maintaining the preset loop offset, the density of the condensate on the mirror surface when the instrument is controlling at the dew point temperature is maintained at its initial value. The operating layer of dew would otherwise be reduced as the contamination level builds up; until eventually the heat pump would be controlled by the contaminant rather than by the condensation. Once the loop contaminant compensation signal parameter has been obtained, the temperature control loop is again closed or enabled. After a short period of time in order to allow the control loop to gain control at the dew point, the previously measured dew point data which was latched into a memory at the initiation of the sequence is erased and up-dated.

DETAILED DESCRIPTION OF THE INVENTION

This invention comprises an improvement of prior art temperature control loop instruments used for dew point measurement. The invention comprises the method and circuitry for interrupting the control loop in order to cause coalescence and subsequent evaporation of the condensate thereby producing the clustered precipitation of water soluble material on the surface of the mirror used in the temperature control loop, and the invention also provides a signal which is injected into the temperature control loop in order to automatically compensate for the reduced reflectance of the mirror because of the contamination contained thereon.

Figure 1:
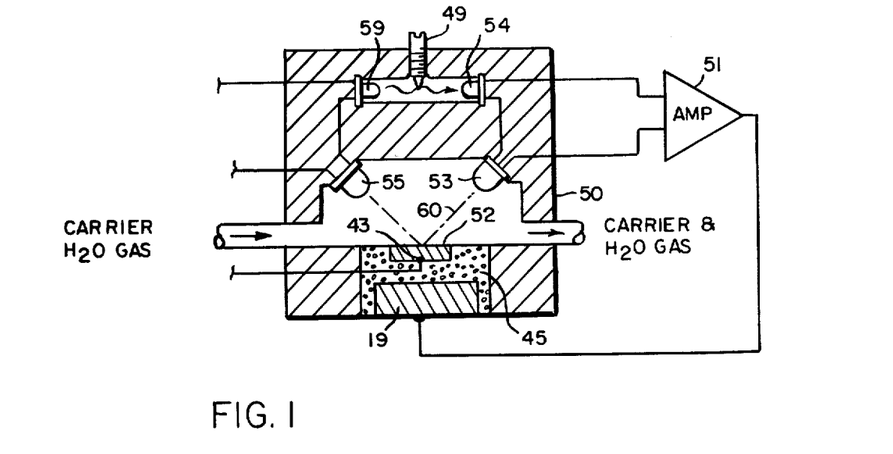
FIG. 1 is a cross-sectional view of the dew-point temperature sensing head.

FIG. 1 shows a cross-sectional view of a dew point temperature sensing head through which the sampled gas passes for determination of water vapor concentration by dew point temperature measurement.

In operation, the condensate detection mirror 52 is illuminated with a solid state, light-emitting diode (LED) 55. A photodetector 53 is configured so as to monitor the specular (direct) component of the light 50 from the mirror. A separate LED 55 and photodetector 54 combination are used to compensate for any thermally-induced changes in the optical components. The photodetector 53 is arranged in the housing 50 such that the specular detector 53 is fully illuminated when the mirror 52 is clear of dew, and sees reduced light as dew forms on the mirror, due to scattering losses.

A provision is incorporated to allow a course balance adjustment of the sensor by the adjusting screw 49. An optical balance is achieved by optical reference adjusting screw 49 in that the signal provided by detector 54 from light source 59 is equal to that provided by detector 53 when the mirror is initially in a clean dry condition. The difference in the output signals of detector 53, 54 is amplified to control the direct current to the thermoelectric heat pump 19 causing the mirror 52 temperature to be at the dew point. As dew begins to form on the mirror, there is a reduction in the specular light 60 to detector 53 which causes a reduction in cooling current 50 to cause the output of pump 19 to decrease. A rate feedback loop within the amplifier 51 is employed to ensure critical response, and the system quickly stabilizes at a mirror temperature wherein a defined density of the dew or frost layer is maintained on the mirror surface, i.e., the dew, or frost point. A precision thermometer element 43 is embedded within the mirror 52 which monitors the dew point temperature of the carrier and $H_2O$ gas directly. The mirror 52 and thermoelectric heat pump 48 are thermally connected by a good thermal conductor medium 45.

Figure 2:
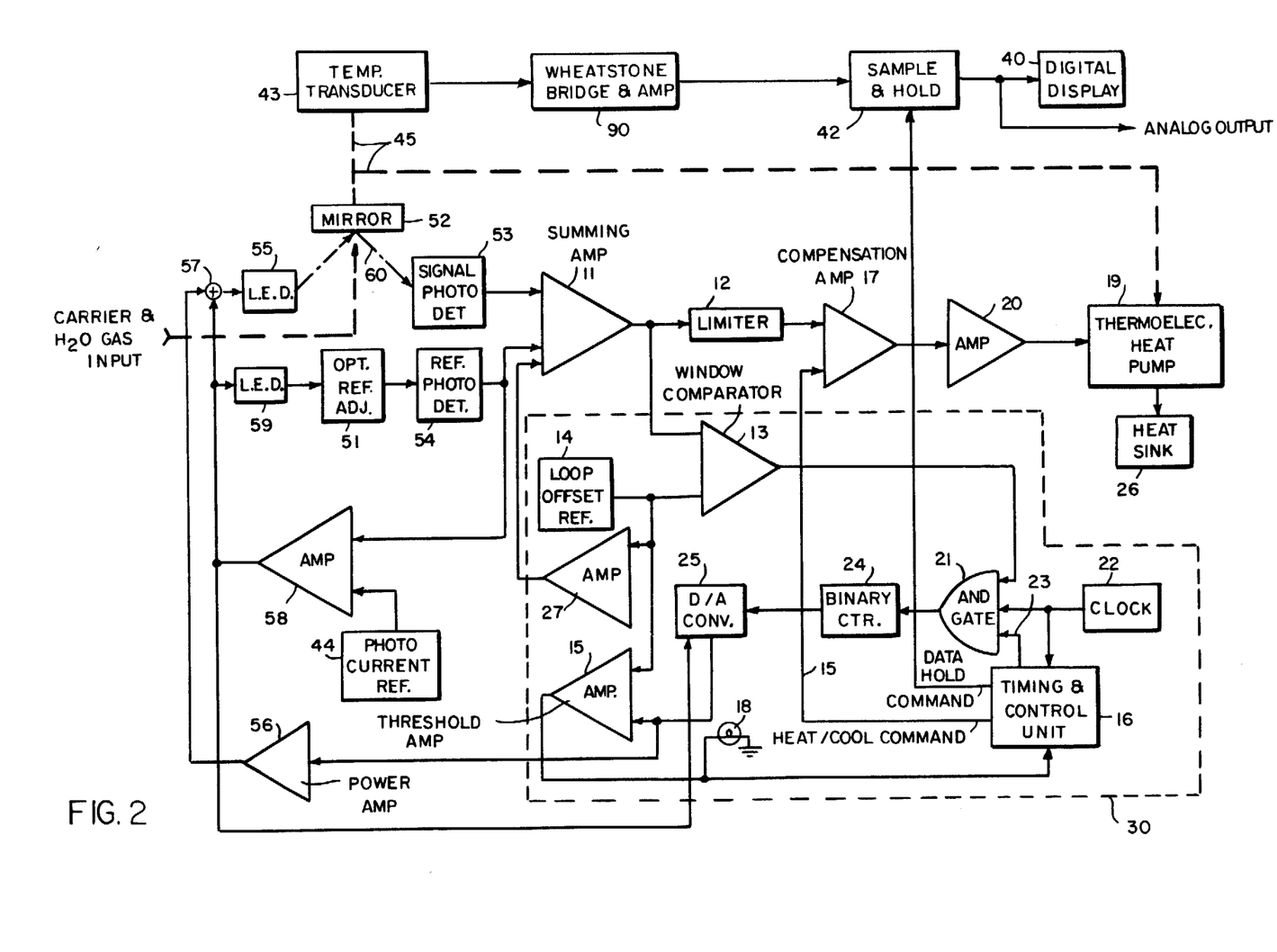
FIG. 2 is a block diagram of a preferred embodiment of the invention.

Referring to the block diagram of FIG. 2 which shows a temperature control system which is controlled and whose operating parameters are adjusted by the present invention, the outputs of signal photodetector 53 and reference photodetector 54 of FIG. 1 are provided as differential inputs to a current summing amplifier 11. When the mirror 52 is clean and dry, the outputs of the photodetectors 53 and 54 are made equal by adjustment of the optical reference adjustment 51. The reference offset voltage 14 is injected into the loop via buffer amplifier 27 so as to cause the thermoelectric heat pump 19, which is in thermal contact 45 with the mirror 52 to pump heat at its maximum rate and thereby slow down the mirror 52 temperature at a predetermined value, normally about 2° C. per second. When the temperature of mirror 52 reaches the dew point, condensation begins to occur on the mirror surface which is illuminated by light-emitting diode 55. The signal photodetector 53, typically a silicon phototransistor, responds to the retro-reflected light which is reduced at the onset of condensation because of light scattering on the mirror 52. When condensation occurs, a difference in photocurrents of detectors 53, 54 results at the input to the current summing amplifier 11 which reduces the amount of current being provided to the thermoelectric heat pump 19. As the dew layer builds up, the drive signal to the thermoelectric heat pump is reduced. A steady state equilibrium condition is reached whereby the mirror temperature is maintained at that point where no further evaporation or condensation occurs. The magnitude of the reference offset 14 establishes the desired density of the operating dew layer as long as other parasitic offset terms, such as changes in mirror reflectance, optical alignment, and thermal drift in solid state devices are nulled. The optimum mean condensate thickness for most applications has been determined to be that which corresponds to a 40 percent reduction in reflectance or photodetector 53 current.

The output of the current summing amplifier 11 provides a voltage at its output which is proportional to the difference in the signal photodetector 53 output and the reference photodetector 54 output. The voltage output of current summing amplifier 11 is provided to a limiter 12 whose output determines the maximum thermoelectric heat pump drive current which occurs while the mirror is dry when slowing down to the dew point. The magnitude of the reference offset required to provide the desired density of the generating dew layer would in the absence of limiting cause overdrive of the heat pump. The output of the limiter 12 is provided as one of the inputs of the compensation amplifier 17 which provides phase lead at the unity gain crossover point of the loop gain characteristic. The compensation amplifier increases the damping ratio of the loop response characteristic in order to prevent excessive ringing or hunting of the servo loop when it comes into control at the dew point.

Near-critical damping is maintained over the entire closed loop operating range of the instrument. Since the heat pump current can safely exceed the average current by a factor of 2½ or more, the heat pump is limited in the steady state only. The current is caused to be larger for transient situations, as will be explained subsequently, in order to provide the desired response.

The output of the compensation amplifier 17 is provided to a power amplifier 20 which drives the thermoelectric heat pump 19. A heat sink 26 is attached to pump 19 as is customary.

The signal phototransistor 53 and reference phototransistor 54 have a common mode operating current level maintained by a feedback controlled network consisting of an operational amplifier 58, one of whose inputs is the output from the reference phototransistor 54 and the other input being a reference voltage from reference source 44. Hence amplifier 58 continuously monitors the common mode phototransistor current of detector 54 comparing it with the reference from source 44 and drives both light emitting diodes 55 and 59. In the event that the reference phototransistor 54 output current starts to drift due to temperature, alignment, or aging effects, the current drive to the light emitting diodes 55, 59 is changed in the direction required to maintain the reference photodetector 54 output current at the preset value.

The temperature of the mirror 52 is measured by the platinum resistance transducer 43, whose resistance is a function of temperature, which is one element of a Wheatstone bridge network and aplifier 90. The Wheatstone bridge is typically of the three wire compensated type known to those skilled in the art, whose differential output drives the input of a precision amplifier circuit whose output voltage is a linear function of the temperature of the platinum resistance element 43. The output voltage of the network 90 is provided to a Sample and Hold circuit 42 which provides an analog voltage output signal and an input to an analog to digital converter 40 which is used to display digitally the temperature of the mirror. The sample and hold circuit 42 is used to provide a steady output dew point reading while the temperature of the mirror is being changed during operations to be described subsequently.

The thermal resistance between resistance element 43 and the mirror 52 surface is such that the temperature differential between the two is small, typically, not exceeding 0.005° C. under maximum heat pumping and sample flow conditions. The resistance of the transducer 43 therefore is truly representative of the mirror 52 surface temperature.

The dew point temperature control loop described above has been modified in this invention to provide circuitry which significantly reduces the problem associated with soluble contaminants on the mirror surface. The effect of soluble contaminants and the countermeasures employed is graphically illustrated in the family of curves in FIG. 3. Curves 3a and 3b are a plot of saturation vapor pressure versus temperature. The vapor pressure of pure water is a function of temperature only. The partial pressure of water in the vapor phase is only a function of the vapor concentration in the carrier gas and the total pressure of the gas mixture. In the absence of water soluble materials, there is a dynamic pressure equilibrium at one unique temperature, which is by definition the Dew Point. In other words, the dew point is that temperature where the saturation vapor pressure of water equals the partial pressure of the vapor with which it is in contact. Because the partial pressure in turn is dependent only on the vapor concentration and the total pressure, if the total pressure is known, the dew point is a true, primary measure of the water vapor concentration. It is, therefore, a superior method of humidity determination. The above arguments hold as long as the gas mixture is in contact with pure water. In some applications, however, water soluble materials exist simultaneously in the gas mixture and the performance advantages of this measurement technique and destroyed. The system of this invention virtually eliminates this problem.

The effect of soluble contaminants are twofold: (1) The mirror reflectance is reduced which tends to diminish the operating dew layer and (2) the vapor pressure of water at any given temperature is lowered in proportion to the mole fraction, (concentration) of solute.

The former has been historically addressed in conventional instrumentation by manual or automatic periodic interruption of the temperature control loop. The interruption has been consistently accomplished by removal of the reference offset voltage. The offset term is necessary when in operation so as to cause the mirror to slew down in temperature and establish the operating density of the dew layer. Removal of the offset voltage allows the mirror temperature to rise so as to evaporate the dew layer. Any remaining offset associated with the reduction of mirror reflectance and other secondary effects, would then be eliminated by injecting an equal and opposite term so as to cause the output of the amplifier to be zero.

The control loop would then be rendered operative be reinjecting the reference offset so as to cause the heat pump to drive the mirror to the dew point temperature. This prior art technique is only partially effective in that it tends to reestablish the operating dew layer, since the layer density decreases as the contamination builds up. The dew layer can be reduced to zero by a sufficient accumulation of foreign matter. Under these conditions, the control loop becomes inoperative in that the system no longer controls on dew.

Balancing the control loop does not however address the problem of measurement error which occurs long before the system goes out of control, if the contaminating material is water soluble.

Figure 3:
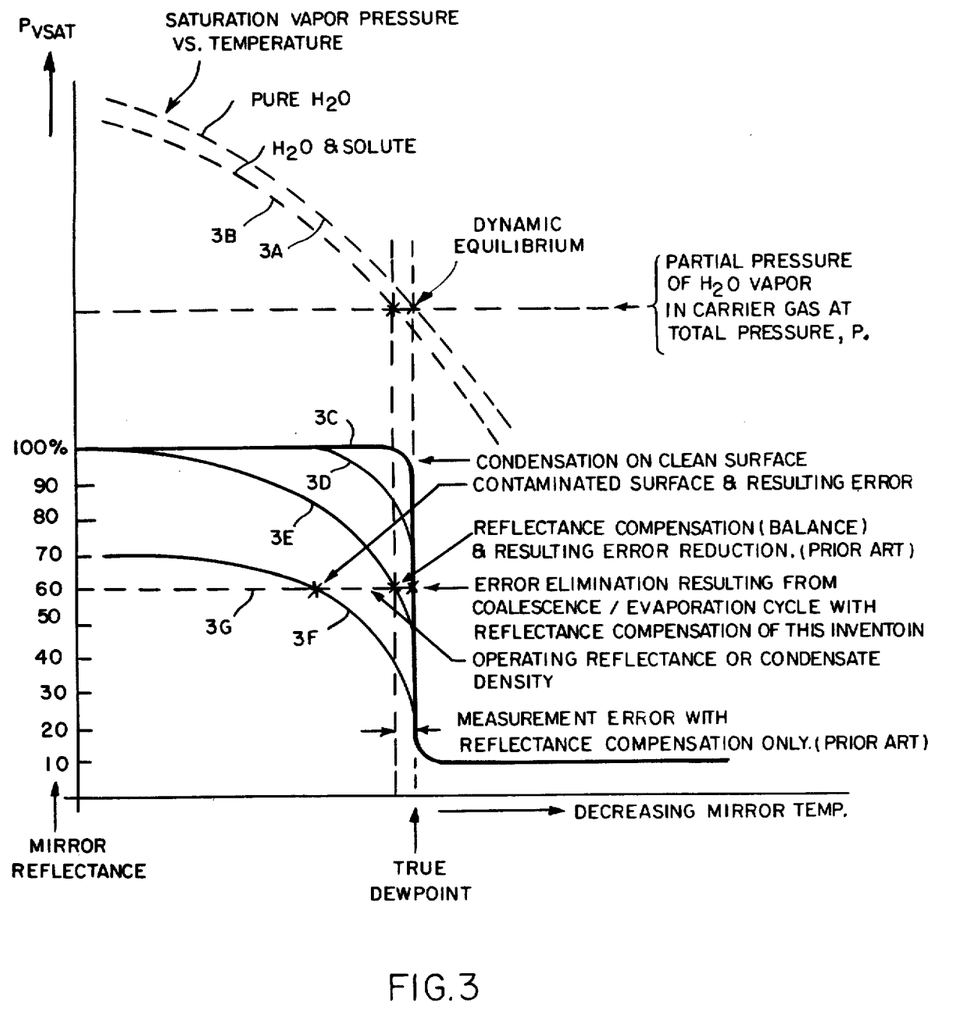
FIG. 3 is a graph of dew point sensor characteristics as effected by water soluble contaminants.

The effect brought about by the presence of solute and the elimination thereof is graphically illustrated in FIG. 3. The effect on vapor pressure is shown in curves 3a and 3b, and its impact on the mirror reflectance versus temperature characteristics in curves 3c–3f. Compensation for the effect of reduction of mirror reflectance by the prior art is illustrated in the curves 3e and 3f. It is evident from these curves that although the dew density is reestablished, there is still a measurement error incurred as a result of the ability of solute to pull water out of the vapor phase at temperatures above the dew point.

The reestablishment by this invention of the reflectance versus temperature characteristic to that which approximates the characteristic of a clean surface is illustrated in curve 3d. The shift in the characteristic curve which is incurred as a result of the clustering or establishment of isolated colonies of solute brought upon as a result of coalescence, evaporation, and reestablishment of the operating dew layer described earlier, clearly illustrates the resulting elimination of measurement error. The achievement of coalescence, evaporation, and reestablishment of the operating dew layer by the instrumentation hardware of this invention produces this effect because that surface area occupied by clustered solute material which becomes optically scattering at temperatures above the Dew Point is a small fraction of the total surface area and cannot therefore reduce the photocurrent by an amount sufficient to establish an operating or control temperature. The substantially larger fraction of clean surface area however can reduce the total reflectance, and therefore the photocurrent, by the amount required to overcome the loop offset or reference, and condensation will occur at this (the latter) clean surface area only at the true dew point. The system is thereby forced to control at the dew point.

Figure 6:
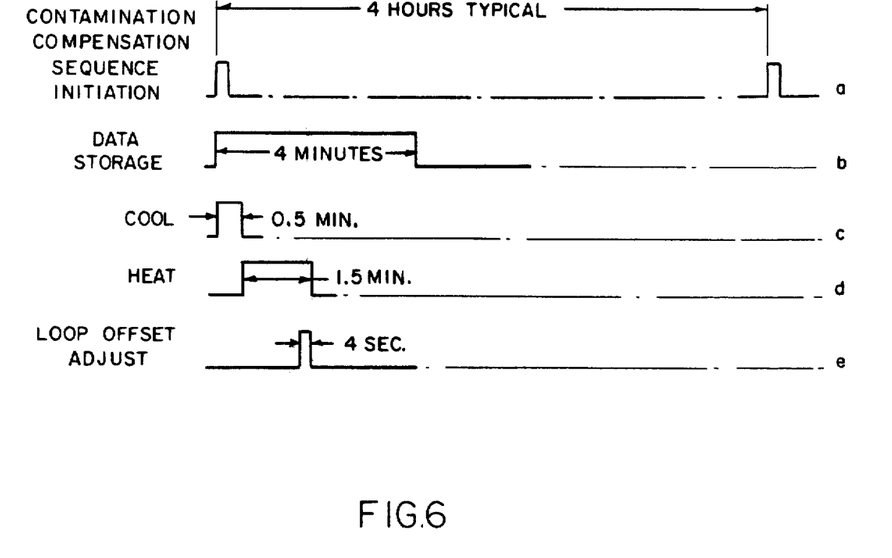
FIG. 6 is a timing diagram of a typical contamination compensation cycle.

The interval between operating cycles of the contamination compensating circuit 30 and the duration of the cycle is determined by the timing and control unit 16. The timing and control unit 16 provides control signals as shown in FIG. 6 whose magnitude is a function of time as determined by clock pulses. Details of the conventional logic circuitry to provide these control signals have not been provided herein since the design of such circuitry is common to those skilled in the design of digital circuitry. A clock 22 provides the timing pulses which causes the timing and control unit 16 to cycle. At a preset time interval (FIG. 6a), the unit 16 will provide a "hold" command (FIG. 6b) signal at one of its outputs to the sample and hold circuit 42. The dew point temperature is represented by the input voltage to the sample and hold circuit 42. During the interval of the hold command signal, the output signal of circuit 42 will be maintained irrespective of the input. In the absence of a hold command, the output of circuit 42 tracks the input. The timing and control unit 16 also provides another signal (FIG. 6c) as one input to the compensation amplifier 17. Initially, the polarity and magnitude of the signal applied to amplifier 17 from circuit 16 is such as to cause amplifier 17 to drive the power amplifier 20 connected to the heat pump 19 to rapidly cool the mirror 52 to a temperature considerably below the dew point. The magnitude of the signal into amplifier 17 from unit 16 overwhelms the signal provided by the limiter 12. Typically, the time for this cooling signal is thirty seconds. The cooling in excess of the dew point temperature causes excess water to deposit on the mirror surface thereby allowing a coalescence to occur on the mirror. The excess of water causes all soluble materials to go into solution.

The coalescence establishes a medium by which ions of solute can migrate. After this excess cooling period, the timing and control circuit 16 provides a "heat" command signal (FIG. 6d) of reverse polarity to the compensation amplifier 17. The heat command signal is of sufficient amplitude and duration to cause the power amplifier 20 to drive the thermoelectric heat pump in reverse which in turn causes the mirror to rise in temperature well above the dew point. This in turn causes the water to evaporate. The excess (coalesced) layer of water breaks up into smaller puddles which continue to break up and shrink in size, holding higher and higher concentration of contaminant in solution leaving bare, uncontaminated surface behind. Each liquid puddle eventually becomes saturated, a nucleation is formed and a polycrystalline cluster grows as the solute precipitates out of solution. The end result is that isolated sites or colonies of contaminants are formed and most of the surface area is left uncontaminated. Water will be pulled out of the vapor phase at temperatures above the dew point only in those regions where cluster of solute are present. Because these areas represent a small fraction of the total surface area, the reduction in photocurrent associated with this phenomenon is not of sufficient magnitude to cause the system to control at temperatures above the dew point. The uncontaminated (substantially larger) surface area on the other hand will accept condensation of water vapor only at the true dew point and because this surface area is much larger, the resulting reduction in photocurrent is sufficient in magnitude to cause the loop to control at the true dew point temperature. The output of the temperature transducer is therefore a measure of the true dew point. This effect is illustrated graphically in FIG. 3.

Because of the amount of total contaminant present on the mirror surface has not been reduced but only redistributed to be as clusters most of the mirror surface is clean but there still exists a reduction in specular reflection because of the clusters. As stated earlier, this tends to reduce the operating dew layer. In order to reestablish the required density of the operating dew layer so that the reduction in reflectance will not reduce the accurary of the dew point temperature measurement, a compensating current is injected into the light-emitting diode 55 by adding in summing circuit 57 a current from a power amplifier 56 to the output of the common mode current injection from LED drive amplifier 58. The input to the power amplifier 56 is provided by the output of a digital to analog converter 25.

The output voltage of the digital to analog converter 25 is determined in the following manner. Just prior to the termination of the heat cycle from the timing and control source 16, the output current from the signal photodetector 53 is less that that which was established initially when the mirror was clean because of the clustered contaminants. Therefore, the output voltage of current summing amplifier 11 is different from that which existed originally. The voltage output of amplifier 11 is compared with the output voltage of offset reference source 14 in window comparator 13. When the output of amplifier 11 is between 4.8 and 5.0 volts typically, and the voltage of reference source 14 is set to 4.9 volts, typically, the output of the window comparator 13 goes "high" and disables "and" gate 21 to which it is connected. The time coincidence of a "low" output from window comparator 13 and a "low" input on line 23 (FIG. 6e) from control unit 16, which occurs a few seconds before the termination of the heat command of unit 16, allows clock pulses from clock source 22 to pass through "and" gate 21 and thereby increment binary counter 24. The count in binary counter 24 remains fixed during the time tht the "and" gate 21 is disabled. The output of the binary counter 24 is provided to a digital to analog converter 25 (where it is multiplied by the common mode current of amplifier 58) whose output drives power amplifier 56 to provide an offset current injection to the signal light emitting diode 55. Thus, the current in the light emitting diode 55 will increase to compensate for the reduction in the reflectance of the mirror until such time as the output of the current summing amplifier 11 falls within the range of window comparator 13 which causes comparator 13 output to go "high" and disable the "and" gate 21 thereby preventing further incrementing of the binary counter 24. The reflectance compensating number in the binary counter at the termination of the incrementing operation remains latched for the duration of the next operating interval.

The reflectance compensating number on the binary counter at the termination of the incrementing operation remains latched for the duration of the next operating interval. Any thermally induced variation in LED drive current required to maintain the desired common mode photodetector current during operation between reflectance compensating cycles, also causes the LED injected reflectance correction term to be adjusted so as not to disturb the reference offset and the operating dew layer. This is accomplished by the multiplying action of the D/A converter 25 inasmuch as the output of the D/A converter is the product of its reference current from amplifier 58 and the input binary number.

The "and" gate 21 enable signal on line 23 from the control unit 16 changes to a state which will disable the "and" gate 21 after a time sufficient to make equal the outputs of detectors 53, 54, typically the enable signal on line 23 is about 4 seconds. The heat command signal FIG. 6d from unit 16 to the amplifier 17 terminates with the enable signal, FIG. 6e. At the termination of the heat command signal, line 15 has no signal on it to affect control of amplifier 17 so that the system is once again in a condition where the closed loop servosystem will take over the automatic cooling of the mirror 52 down to the dew point temperature.

After an extended period of time a subsequently described indicator alerts the operator that the mirror must be cleaned. After the mirror has been cleaned, the inputs to the summing amplifier 11 in the temperature control loop will be greatly imbalanced because the number which provided the correction signal for the loss of reflectance of the mirror because of the contamination is still stored in the binary counter 24. Therefore, the output of the current summing amplifier 11 will be outside of the window of the comparator 13 thereby causing its output to be "low" to provide an enabling signal to the "and" gate 21. The signal on line 23 is caused to enable the "and" gate 21. Therefore, the binary counter 24 will count through its maximum count, back to zero, and back up again until the output of current summing amplifier 11 once again falls within the window of the comparator 13. At that time, the "and" gate 21 will be disabled and the system will be in condition for closed loop temperature control.

As the mirror contamination increases, the amount of compensating signal provided by amplifier 56 after each operation of the contamination compensating circuitry increases to compensate for the reduced reflectance of the mirror. A comparator circuit 15 is used to provide energization to a warning light 18 when the mirror contamination has reached a point where it should be cleaned. The inputs to the comparator 15 are the reference voltage from source 14 and the output of the amplifier 58. When the output of amplifier 56 exceeds a predetermined amount, the comparator 15 output will change state to provide energization to the warning light 18 and also a signal to the timing and control unit 16. While the signal from comparator 15 is being provided to unit 16, a "hold" command signal will continue on the sample and hold circuit 42 so that the indicated temperature cannot change until such time as comparator circuit 15 reverts to the original state indicating that the output of power amplifier 56 is a low value corresponding to a clean mirror.

Although offset correction can be achieved by current injection directly into the control amplifier 11, common mirror reflectance compensation by control of the source (LED) intensity is superior because the signal photodetector current is maintained even though the optical transmission of the signal channel has been reduced by the presence of contaminant on the mirror. This in turn tends to ensure temperature tracking of the photodetectors and maintain the operating point of the signal photodetector in the center of its dymanic range, so that the operating current does not reduce to the cut off point when dew is formed on a heavily contaminated surface. It also is superior in that the initial (clean mirror) density of the operating dew layer is maintained.

Figure 4:
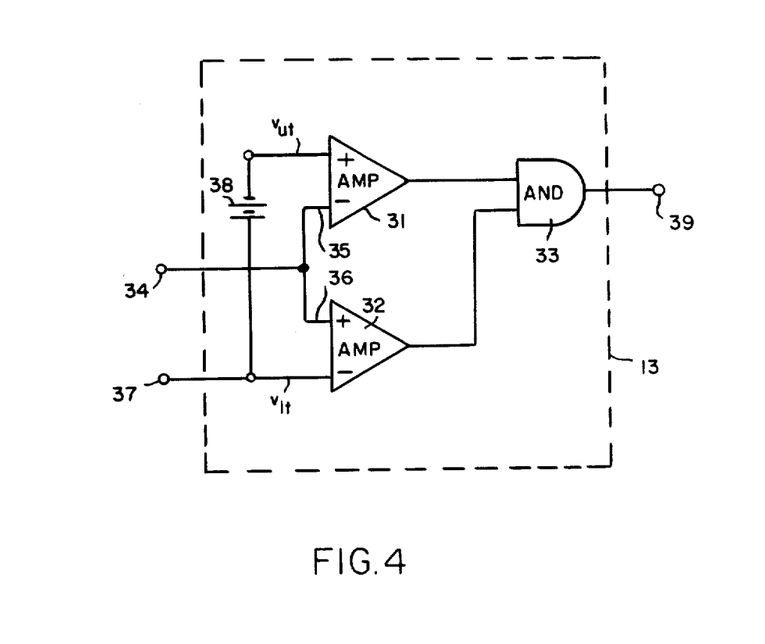
FIG. 4 is a circuit diagram of a window comparator.

The window comparator 13 of FIG. 2 comprises, as shown in FIG. 4, two voltage comparators 31 and 32 whose outputs are provided as inputs to "and" gate 33. The signal from current summing amplifier 11 is provided to input 34 of the window comparator which in turn is connected to complimentary terminals 35, 36 of the voltage comparators 31, 32, respectively. The reference voltage from source 14 is applied to terminal 37 of the window comparator which is in turn connected to the remaining input terminal $v_{lt}$ of comparator 32 and through a 0.2 volt offset voltage source 38 to the remaining terminal $v_{ut}$ of comparator 31. When the voltage V in at terminal 34 is between the voltage $v_u t$ (upper threshold voltage) and $v_{lt}$ (the lower threshold), the output voltage $V_O$ at terminal 39 is high. For all other relationships of the input voltage with respect to the threshold voltages, the output at terminal 39 is low.

Figure 5:
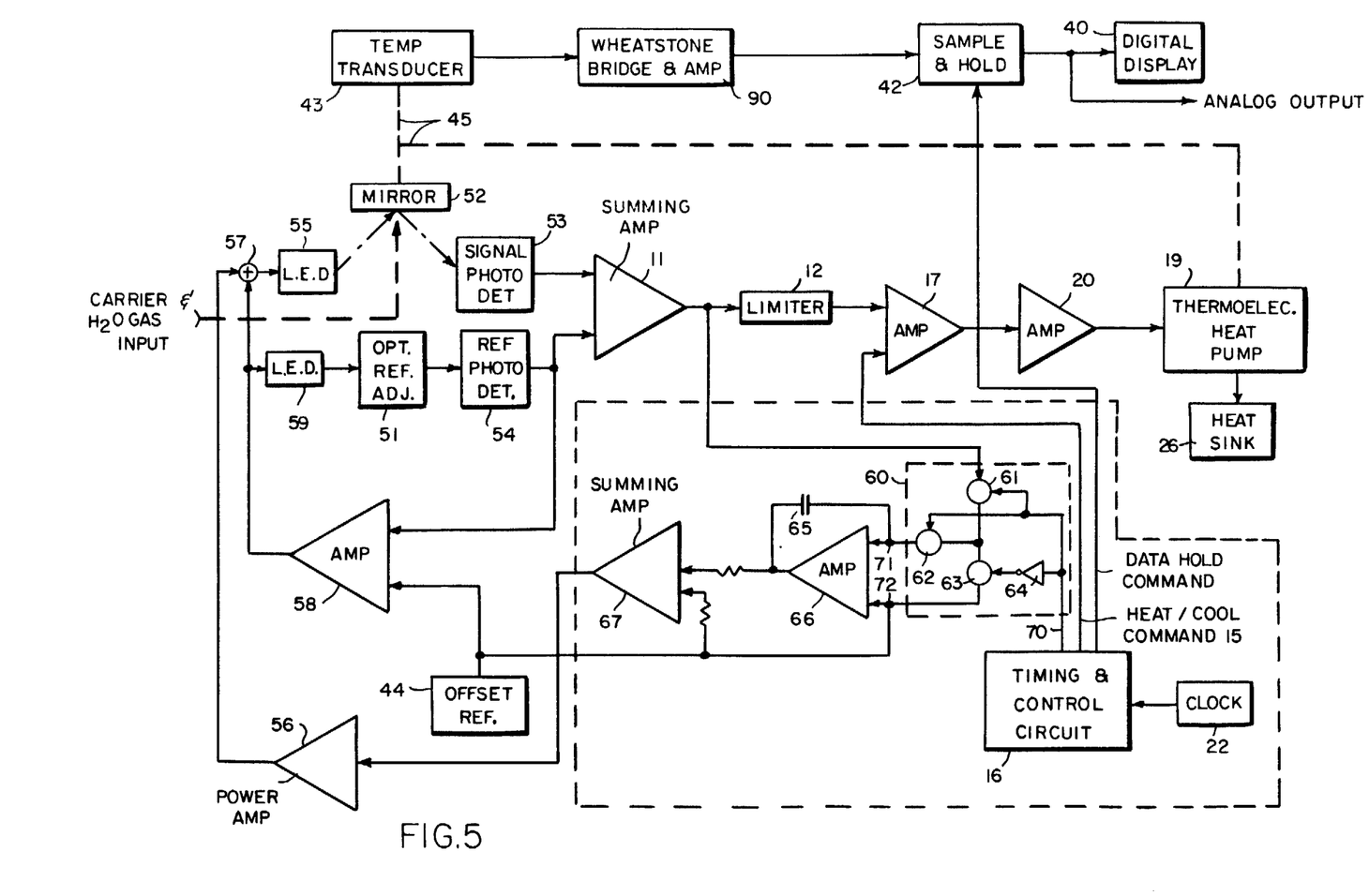
FIG. 5 is a block diagram of another embodiment of the invention.

The circuit of FIG. 5 may be used where sequence programmability and the accuracy produced by the digitally controlled reference signal which compensates for the mirror contamination are not required, and a less expensive compensation circuit than that of FIG. 2 is adequate.

As with the digital system previously described, upon the initiation of the coalescence command by the timing and control unit 16, the dew point measurement is latched by the data "hold" command signal provided by the timing and control unit 16 to the sample and hold circuit 42. The signal on line 15 cools the mirror for a half minute, and then is reversed in polarity to heat the mirror for one and a half minutes.

Prior to the termination of the heat command signal, a signal (FIG. 6e) is provided on line 70 from timing and control circuit 16 to switch 60 which connects the output of the current summing amplifier 11 to one input 71 of an operational amplifier 66 whose other input 72 is connected to reference source 44. The output of the operational amplifier 66 is summed with the voltage of reference source 44 at the input of amplifier 67. The output of amplifier 67 is provided as an offset current to the signal LED 55 to slow the output voltage of amplifier 11 to the voltage of source 44, typically 4.9 volts, so that the inputs to the operational amplifier 66 are nearly equal.

After a time sufficient for the output of current summing amplifier 11 to assume a value equal to that of the reference voltage from source 44, but prior to the time that the heat command is removed by control unit 16 the signal 70 causes switch 60 to disconnect the output of current summing amplifier 11 from the input of operational amplifier 66. The voltage at the output of amplifier 66 continues to be applied by the action of storage capacitor 65 which has been charged during the time that the input switch 60 to amplifier 66 has been closed.

Therefore, the correction signal required to offset the contamination of the mirror is provided during the normal operation wherein the correction term is maintained by the storage of voltage on the storage capacitor 65. The switching circuitry which controls the connection of the output of the current summing amplifier 11 to the input terminal 71 of the amplifier 66 is provided by MOS-FET transsistors 61 and 62. These transistors are turned "on" and "off" by the signal on line 70. Because the leakage resistance of these transistors when in the off-state is only $10^6$ ohms, the circuit has been modified to provide a third FET transistor 63 which is driven by an inverter 64 such that transistor 63 is "off" when transistors 61 and 62 are "on" and vice-versa. Transistor 63 is connected between the junction of the transistors 61 and 62 and the reference source 44.

The voltage across switch 62 when in the open or "off" state is therefore zero. This in turn forces the current in the leakage resistance of switch 62 to zero thereby eliminating the remaining major source of parasitic current in the storage capacitor. Since the MOS-FET amplifier 66 input bias and leakage current is of the order $10^{-11}$ amperes, the net effect is that the voltage drift on the storage capacitor (approximately 10 mv/hr) is reduced to a level which is adequate for this application. The storage capacitor 65 is a low leakage capacitor. A Mylar capacitor having a leakage resistance of $10^{12}$ ohms is satisfactory.

Reflectance correction circuit is enabled by closing switches 61, 62 and opening 53 so as to change capacitor to that point where LED 55 drives summing amplifier 11 output 22 in photodetector 53 to the amount of the reference voltage.

Reflectance correction circuit is disabled by opening switches 61, 62 and closing 63 so as to prevent any further changing or discharging action in the storage capacitor by opening the changing current path via mode 71 and thereby maintaining or storing the reflectance connection voltage for the duration of the next dew point measurement interval. The switching scheme employed utilizes complimentary symmetry metal oxide, silicon, Field Effect Transistors, (CMOS FET's) integrated into a single package.

The switch arrangement overcomes the parasitic leakage resistance (approx. $10^6$ ohms) which exits across these solid state switching devices when in the open state in the following manner.

In accordance with fundamental axioms relating to operational amplifiers, the voltages at nodes 71 and 72 are very nearly equal, i.e., the difference is equal to the output voltage (5-10 volts) divided by the open loop gain of the device (approx. $10^6$). The above argument presumes that any input offset voltage on the device has been nulled.

As stated, switches 61 and 62 are closed and switch 63 is open when in the storage or hold state.

Any change in the input voltage from amplifier 11 (which occurs when the temperature control loop is operative) relative to the reference voltage is dropped across switch 51 (approx. $10^6$ ohms) since it is open and 63 is closed (approx. 100 ohms).

The voltage dropped across 62 is therefore reduced by a factor equal to the ration of the "on" resistance of 63 to the "off" resistance of 61 (approx. $10^{-4}$). The voltage across the leakage resistance of 62 is therefore of the order of $10^{-4}$ which reduces the leakage current through switch 62 to less than $10^{-10}$ amperes. The resulting drift rate on the capacitor is of the order of $10^{-5}$ volts per second or 0.01 V. per hour, worst case, which is sufficient for this application.

It is evident that those skilled in the art, once given the benefit of the foregoing disclosure, may make numerous other uses and modifications of, and departures from the specific embodiments described herein without departing from the inventive concepts. Consequently, the invention is to be construed as embracing each and every novel combination of features present in, or possessed by, the apparatus and techniques herein disclosed and limited solely by the scope and spirit of the appended claims.

What is claimed is:

1. A dew point hygrometer for determing the dew point of a gas sample, of the type having:
   a mirror having a reflective surface exposed to the gas sample,
   a light source for directing a beam of light upon the reflective surface of the mirror,
   cooling and heating means in heat exchange relation with the mirror,
   a photosensitive means responsive to light reflected from the surface of the mirror,
   servo loop control means interposed between the photosensitive means output and the cooling means for maintaining the temperature of the mirror at the dew point of the gas sample,
   wherein the improvement for reducing or eliminating dew point measurement error due to vapor pressure modification as induced by the presence of soluble contaminant on the reflective surface of the mirror comprises,
   means for periodic interruption and disabling of the servo loop control means, for purposes of, and for causing said cooling means to cool said mirror to a temperature sufficiently below the dew point to cause coalescence of the condensate so as to form a film of water in order to totally dissolve the solute on the surface of said mirror and for subsequently causing said heating means to heat said mirror thereby permitting the mirror temperature to rise causing the water to evaporate and the solute to precipitate or crystallize in isolated colonies or aggregate clusters and to dry said mirror leaving areas of said mirror base of solute,
   means for reflectance measurement from said mirror after total evaporation and redistribution of solute to establish the level of compensating signal to compensate for the reduction of said mirror reflectance by said precipitated solute, and means for providing said compensating signal to the servo loop control means in such a manner as to provide for a predetermined constant density of condensate on the reflective surface after reverting back to normal operation, thereby causing undisturbed growth of condensate on bared regions between aggregates of soluble material so as to maintain mirror temperature control at the true dew point of the gas sample, means for enabling said servo loop control, after said compensation signal has been provided, to control the temperature of said mirror at the dew point temperature, means for temperature compensating said photosensitive means to provide a current component in its output which is constant with temperature change of the photosensitive means, said temperature compensating means making the dew density unaffected by temperature.

2. The apparatus of claim 1 wherein said means for providing a compensation signal in such a manner as to cause a constant dew density when in normal operation independent of contamination level comprises means for providing a reference signal, means for comparing a signal from the photosensitive means when said mirror is dry to a signal from said reference signal means to provide a comparison signal, means for storage and amplification of the comparison signal from said comparing means to provide said compensation signal during normal operations, said temperature compensating means providing a driving signal, means for summing said compensating signal with said driving signal to said mirror illuminating light source means for the purpose of increasing the intensity of said light source in proportion to the reduction in reflectance of said mirror by the contaminating material.

3. The apparatus of claim 1 wherein said means for disabling the servo loop control comprises means for introducing a first signal into said servo loop control to force the cooling means to cool said mirror below the dew point, a heating means in heat exchange relation with the mirror, means for introducing a second signal subsequent to the termination of said first signal into said servo loop to force the heating means to heat said mirror above the dew point temperature.

4. The apparatus of claim 3 wherein said heating means and said cooling means are provided by a thermoelectric heat pump, said first signal is of a polarity to cause said pump to cool, and said second signal is of the opposite polarity to cause said pump to heat.

5. The apparatus of claim 1 comprising in addition timing means enabling the periodic means and reflection measurement means at predetermined time intervals for a predetermined time duration.

6. The apparatus of claim 1 wherein said means for providing a compensation signal comprises means for comparing said offset reference voltage with an offset voltage in said servo control loop to provide a signal of one polarity when said loop offset voltage and off-set reference voltage are different by a predetermined amount and a voltage of the other polarity otherwise, a binary counter, means for increasing the count of said binary counter in response to said one polarity of voltage when said mirror is dry, means for converting the count of the counter to a corresponding analog voltage to provide said compensation signal, said compensation signal when introduced into said servo control loop causing said servo control loop offset voltage to be equal to said offset reference voltage within said predetermined amount, means for maintaining and continuing to provide said analog voltage compensation signal when said servo control loop is cooling said mirror at the dew point temperature, and means for providing a common mode current to said light source, a fraction of said common mode current being provided to said digital to analog converter as a reference current which establishes the full scale output current of said converter.

7. The apparatus of claim 6 wherein said comparing means is a window comprator.

8. The apparatus of claim 1 wherein said means for providing a signal to the servo loop to provide a predetermined density of condensate comprises a loop offset reference voltage source to provide a voltage, means for providing said reference voltage to said servo control means to cause said cooling means to cool said mirror to the dew point so as to cause the signal from said photosensitive means to decrease by an amount equal to the offset reference voltage because of an increase in condensate thickness.

9. The apparatus of claim 1 wherein said means for temperature compensation of said photosensitive means comprises a reference light source, a reference photosensitive means illuminated by said second light source, means for maintaining said light source and both said photosensitive means under the sane environmental conditions, a photocurrent reference voltage source, means for comparing the reference photosensitive means output voltage with said reference voltage and for providing energization to said reference light source to maintain the output voltage of said reference photosensitive means fixed respect to said reference voltage, said energization means also providing equal energization to the light source for the mirror.

10. The apparatus of claim 9 wherein said compensation signal provided in said servo loop is provided as an additional energization signal to the light source for said mirror.

11. The apparatus of claim 1 wherein said means for providing a compensation signal comprises an operational amplifier, a switch connected to said servo control loop and one input of said operational amplifier, a capacitor connected between said input and the output of the operational amplifier, an offset reference voltage source, the other input of said operational amplifier being connected to the said offset reference voltage source, the output of said operational amplifier being connected to said light source to connect said compensation signal to said servo control loop to compensate for the contamination of said mirror, means for closing said switch during the time said mirror is dry, said capacitor acquiring a charge while said switch is closed, opening said switch prior to allowing said loop to begin to cool said mirror, said capacitor continuing to provide said compensation signal while said servo control loop is maintaining the mirror at the dew point temperature.

12. A method for use in condensation hygrometry for redistributing soluble contaminant into concentrated clusters on the condensing surface thereby removing contaminating material from most of said surface which is used for the determination of the temperature of condensation of a vapor constitutent of a gas comprising, periodically interrupting normal temperature control of the condensing surface and, cooling said surface below the condensation temperature for a time sufficient to cause the condensate to coalesce and form in sufficient quantity to develop a liquid film which is capable of dissolving all of the solute material on said surface, heating said surface for a time and to a temperature sufficient to evaporate said liquid film of solvent thereby causing said soluble contaminants to precipitate out of solution and cluster in isolated colonies on said surface.

13. In a method for determining the condensation temperature of a vapor contained in a gas sample of a type wherein the temperature of a surface is maintained at the condensation temperature by a temperature control liip, and wherein said surface is responsive to the liquid on its surface to provide a control signal to said loop, the improvement which eliminates the solute induced measurement error comprising the steps of, disabling said temperature control loop, cooling said mirror below the condensation temperature to a temperature and for a time sufficient to cause the liquid droplets of said vapor to coalesce and dissolve all of the existing solute and form an extended sheet of liquid solution on said surface, heating said surface above the condensation temperature to a temperature and for a time sufficient to evaporate said liquid from the surface causing precipitation of solute material in clusters or isolated colonies, thereby removing solute material from most of the surface area of said mirro, establishing the magnitude of the reflection compensating signal while the contaminated mirror is dry, storing that magnitude, injecting said reflection compensating signal into the temperature control loop so as to maintain the loop offset which establishes the required density of the operating dew layer to compensate for any change in control signal caused by contamination on said mirror, providing a signal corresponding to the environmental temperature and injecting said signal into the control loop to compensate for any change caused by change in said environmental temperature to maintain the required density of operating dew layer, enabling said temperature control loop and cooling said surface to its vapor condensation temperature by said temperature control loop with said compensating signal continuing to be provided to said control loop.

14. In a method for automatically measuring the dew point of a carrier gas plus water vapor of the type where the temperature of a mirror is automatically controlled at the dew point by a temperature control loop wherein the mirror is cooled in response to the signal provided from a photodector by light which is reflected from said mirror from a light source, the improvement which eliminates the solute induced measurement error comprising the steps of, periodically disabling the mirror temperature control loop, cooling said mirror to a temperature below the dew point to a temperature and for a time sufficient to cause the dew droplets to coalesce and form an extended sheet of water on the surface of said mirror, heating said mirror above the dew point to a temperature and for a time sufficient to evaporate said water from the surface of said mirror and to dry said mirror, establishing the magnitude of the reflectance signal while the contaminated mirror is dry, storing that magnitude, injecting said reflectance compensating signal in the temperature control loop so as to maintain the loop offset which establishes the required density of the operating dew layer to compensate for any change in control signal by contamination on said mirror, and then cooling said mirror to its dew point temperature by said temperature control loop with said compensating signal continuing to compensate for any mirror reflectance change.

15. The method of claim 14 wherein said reflectance compensating signal is provided to the temperature control loop through said light source to cause the signal obtained by the reflective light of said dry mirror to be substantially the same as the signal from said mirror when in its initial clean and dry state, thereby maintaining the operating point of the photosensitive detector and providing the means for maintaining a constant dew density independent of contamination level.

* * * * *